(12) United States Patent
Hebert et al.

(10) Patent No.: US 7,993,302 B2
(45) Date of Patent: Aug. 9, 2011

(54) CLOT RETRIEVAL DEVICE

(76) Inventors: Stephen Hebert, San Francisco, CA (US); Marc-Alan Levine, Pottstown, PA (US)

( * ) Notice: Subject to any disclaimer, the term of this patent is extended or adjusted under 35 U.S.C. 154(b) by 663 days.

(21) Appl. No.: 11/800,367

(22) Filed: May 3, 2007

(65) Prior Publication Data

US 2008/0065012 A1  Mar. 13, 2008

Related U.S. Application Data

(60) Provisional application No. 60/799,055, filed on May 9, 2006.

(51) Int. Cl.
*A61M 31/00* (2006.01)
*A61M 37/00* (2006.01)

(52) U.S. Cl. .................................................. 604/103.08
(58) Field of Classification Search ............. 604/103.08
See application file for complete search history.

(56) References Cited

U.S. PATENT DOCUMENTS

| | | | | |
|---|---|---|---|---|
| 3,635,223 A | * | 1/1972 | Klieman | 606/194 |
| 5,624,450 A | * | 4/1997 | Glastra | 606/108 |
| 6,685,722 B1 | * | 2/2004 | Rosenbluth et al. | 606/200 |

* cited by examiner

*Primary Examiner* — Nicholas D Lucchesi
*Assistant Examiner* — Pritesh Patel

(57) ABSTRACT

A device for removing material from a patient's body comprising a shaft and an adhesive carrying surface extending from the shaft. The adhesive carrying surface is movable with respect to the shaft and has an adhesive on at least a portion of its outer surface. The adhesive has sufficient stickiness to adhere to a body material to remove the material when the shaft is removed from the patient's body.

17 Claims, 13 Drawing Sheets

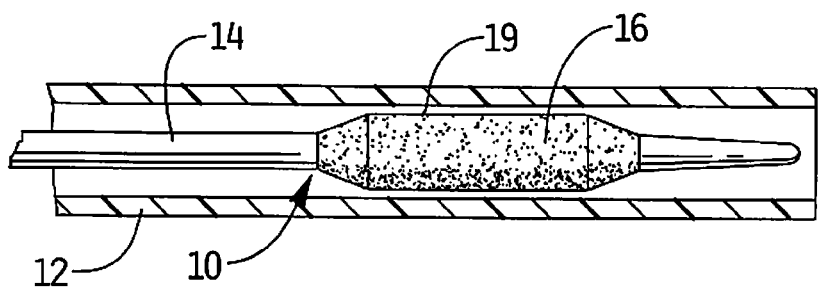
FIG_1A
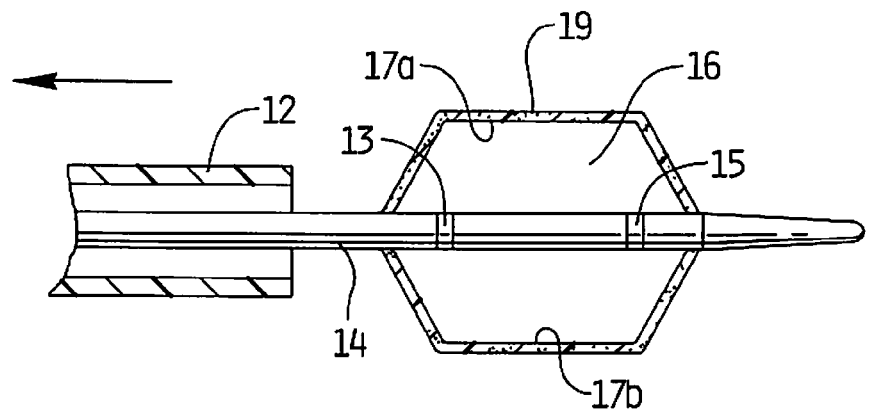
FIG_1B
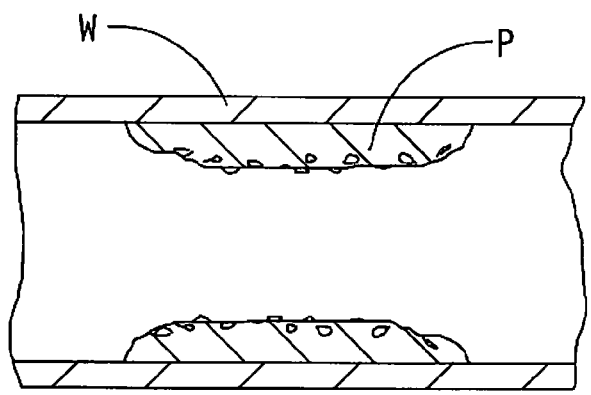
FIG_1C

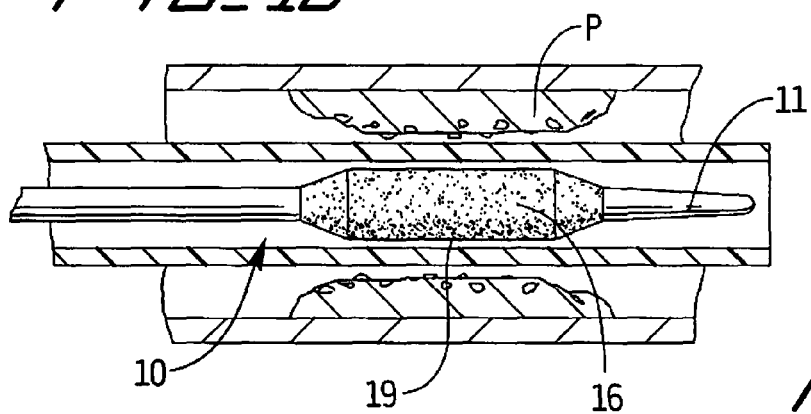
FIG_1D
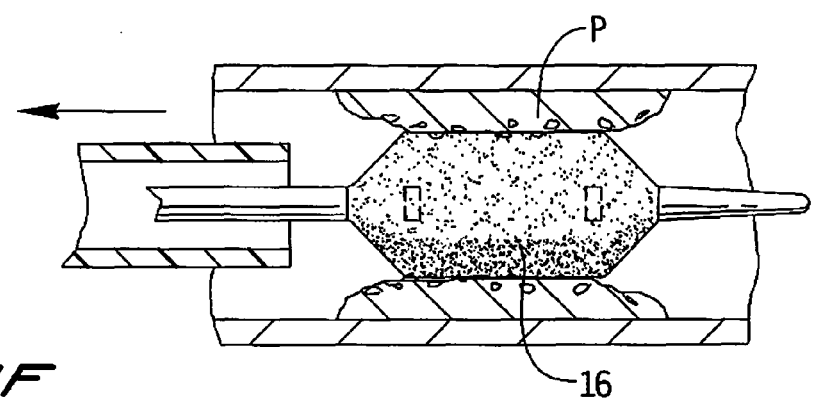
FIG_1E
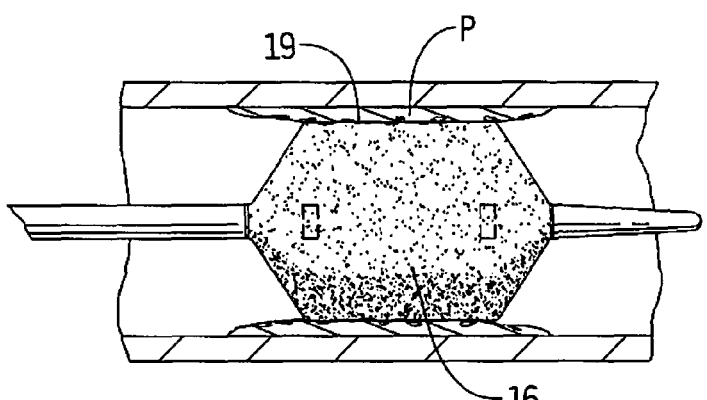
FIG_1F
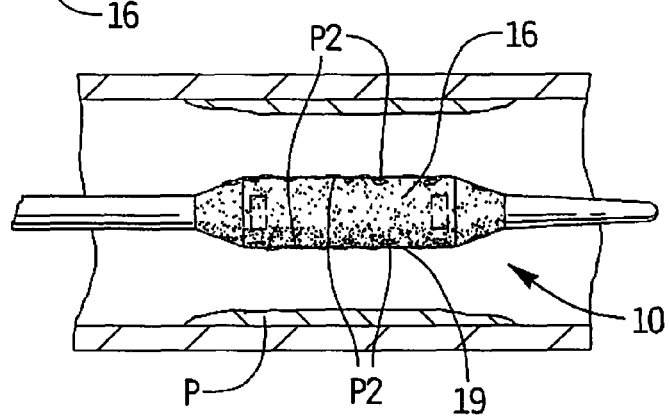
FIG_1G

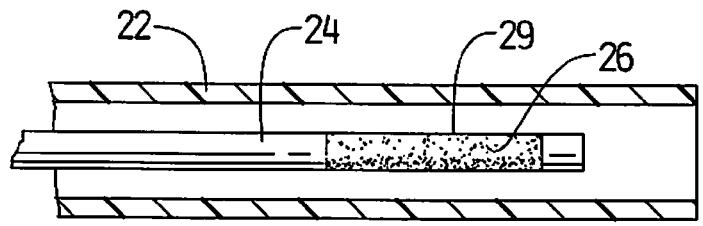
FIG_2A
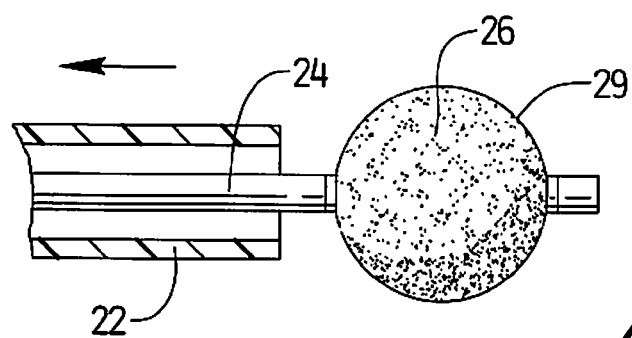
FIG_2B
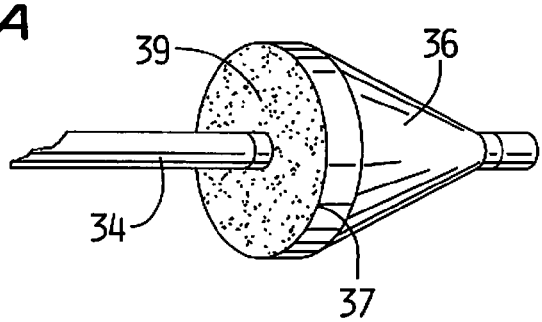
FIG_3A
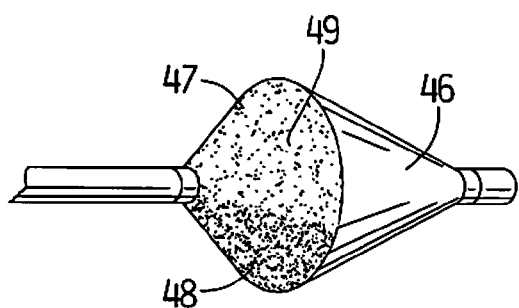
FIG_3B

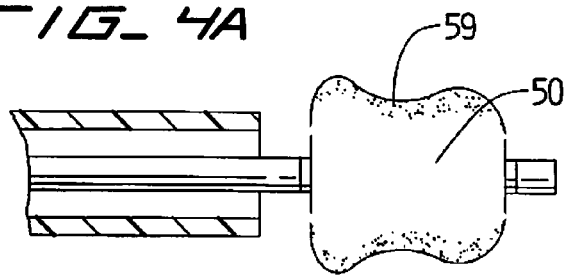
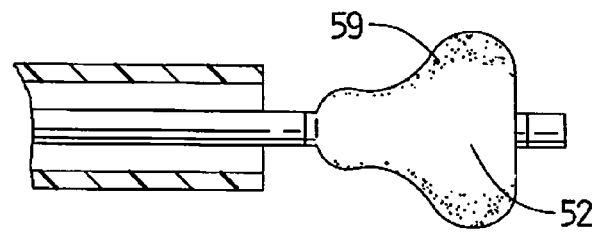
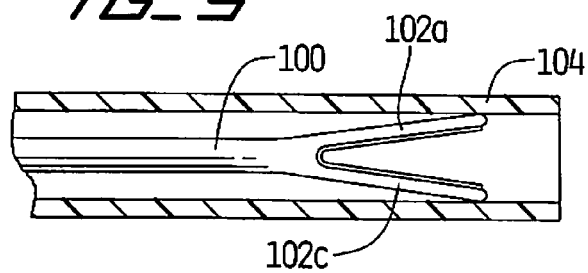
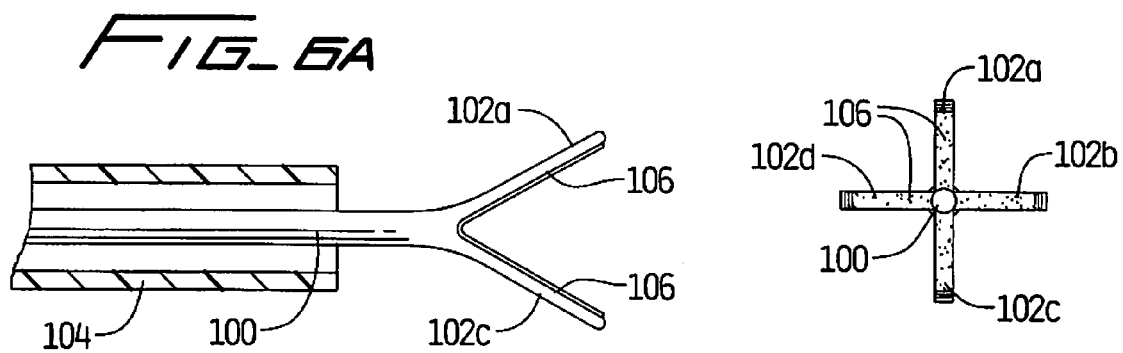
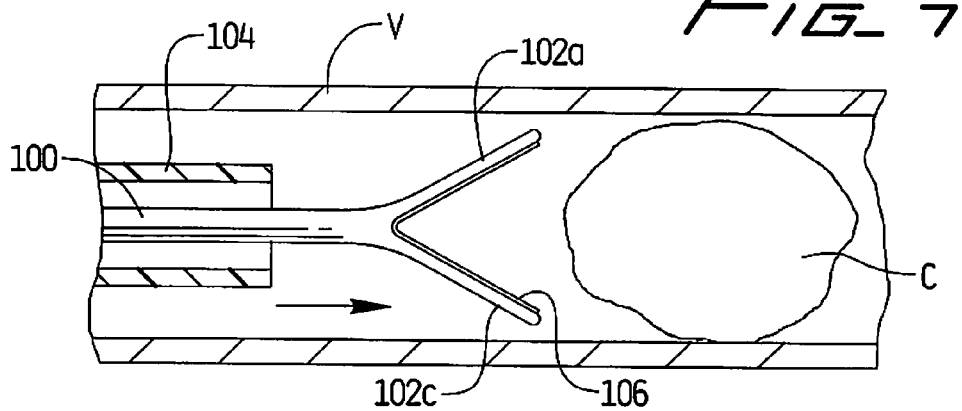

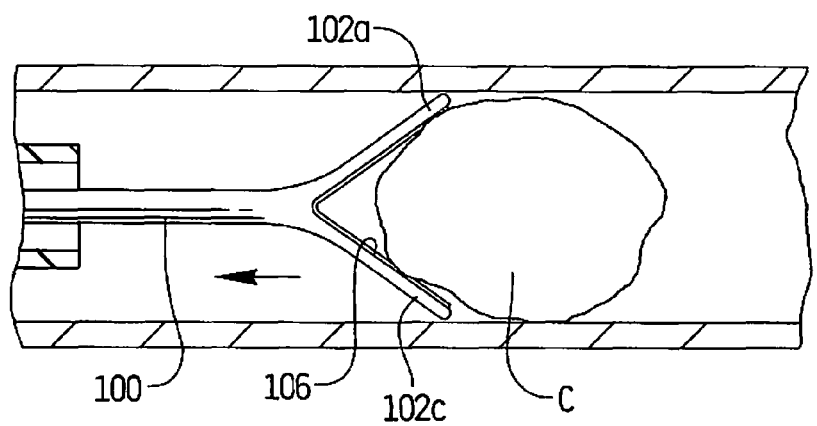
FIG_8
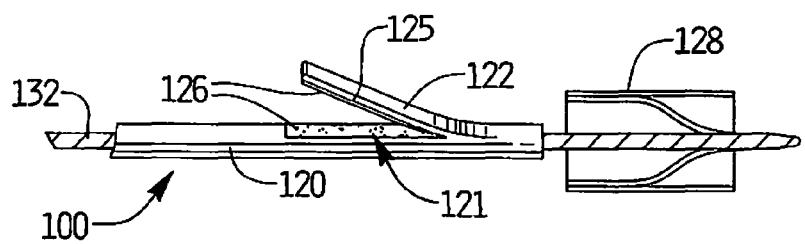
FIG_9A
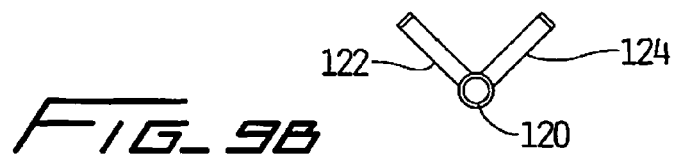
FIG_9B
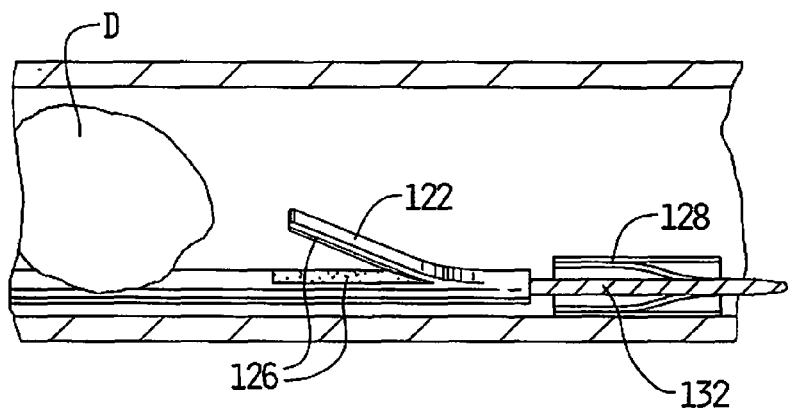
FIG_10

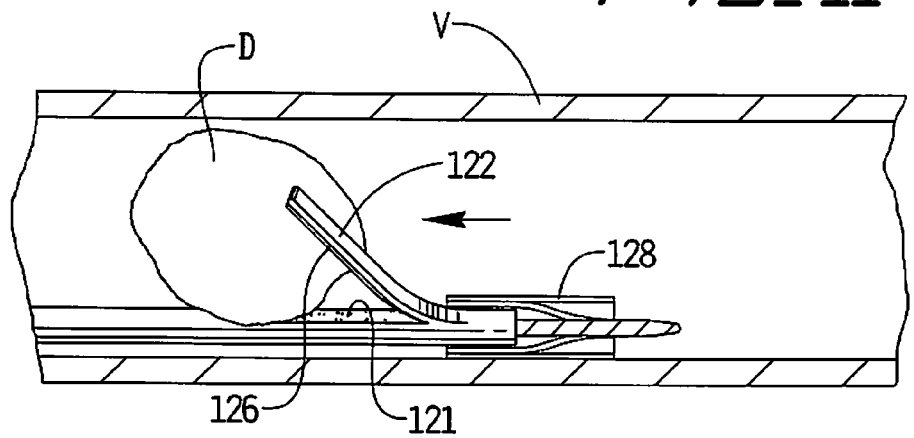
FIG_11
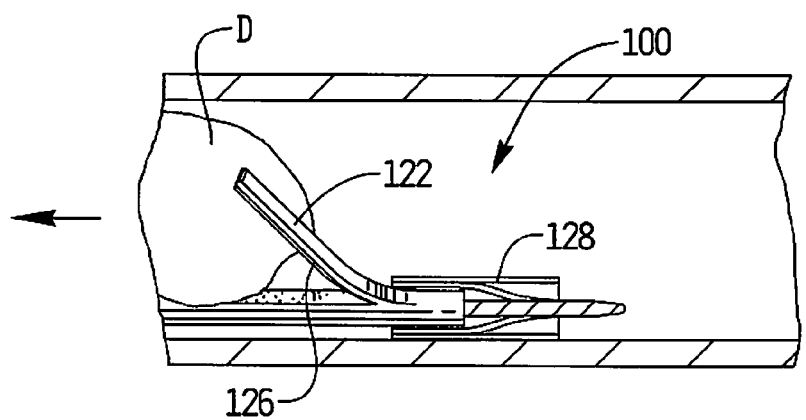
FIG_12
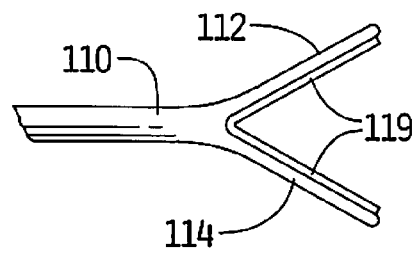
FIG_13A
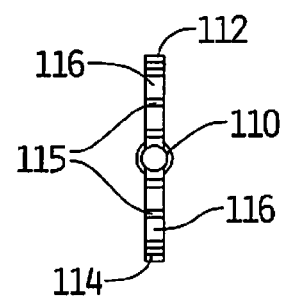
FIG_13B

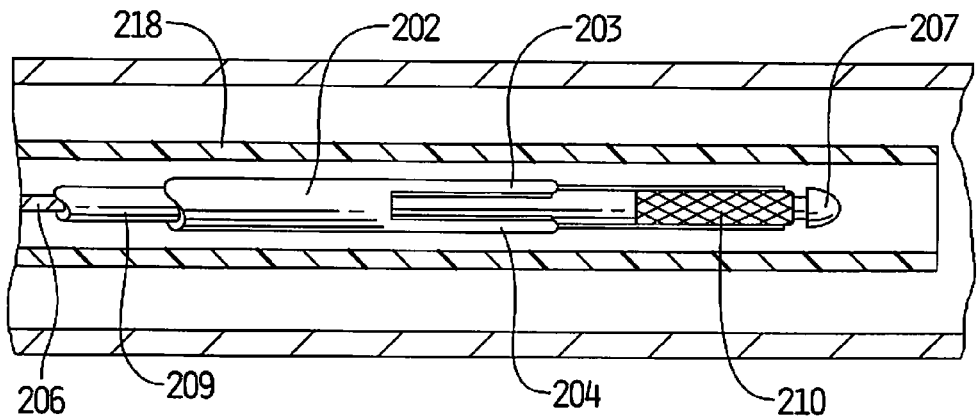
FIG_14A
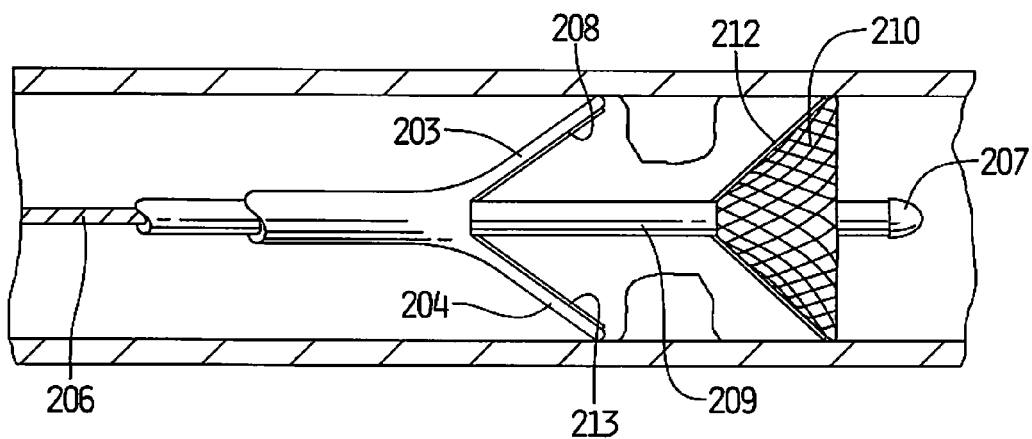
FIG_14B
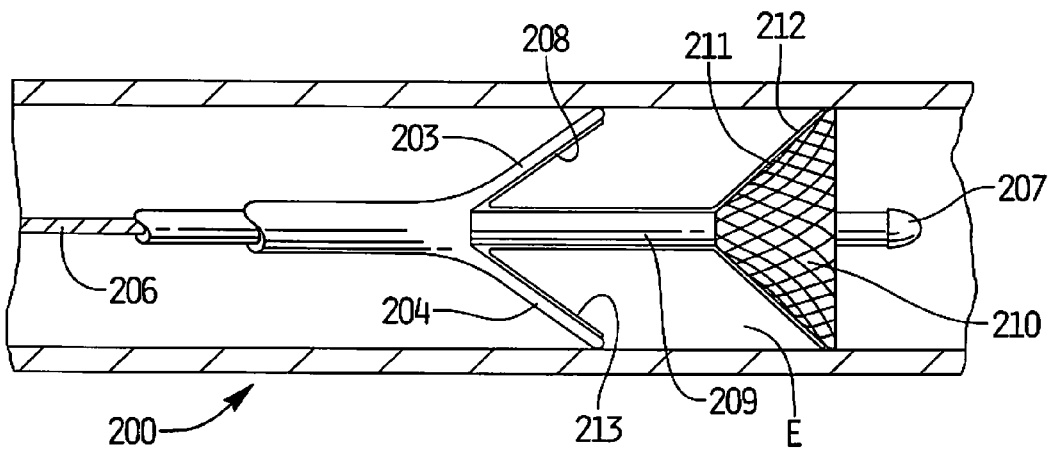
FIG_14C

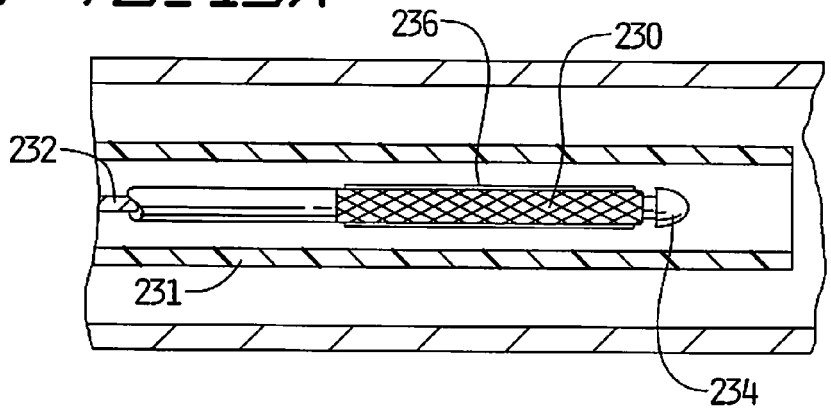
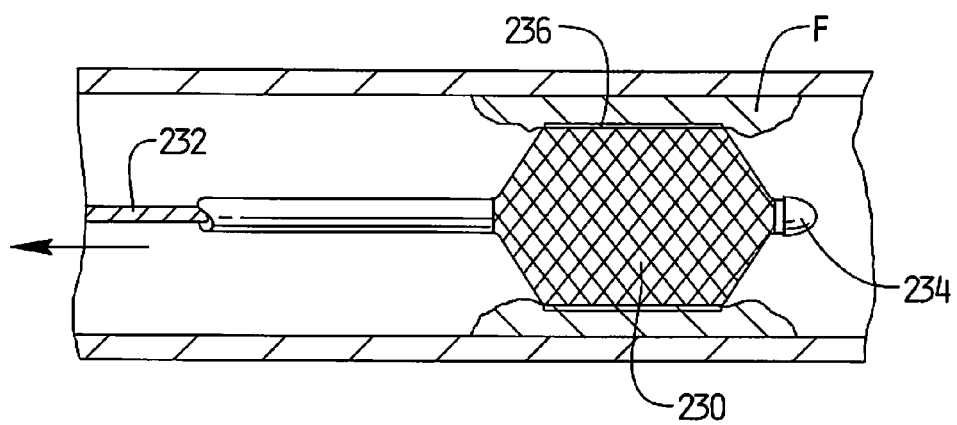
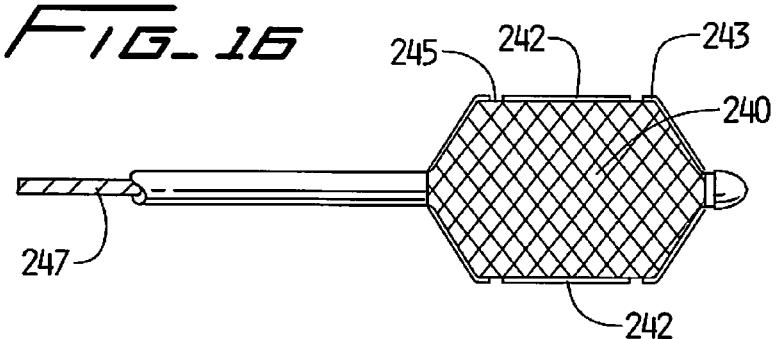
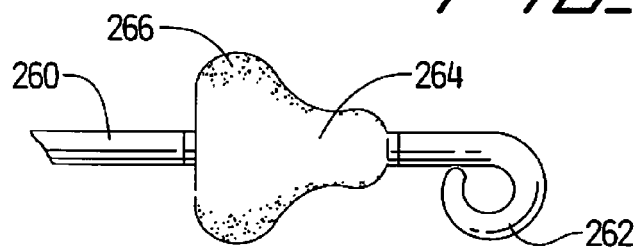

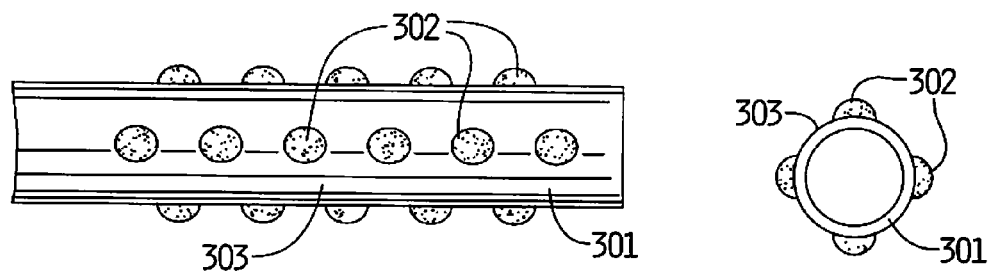
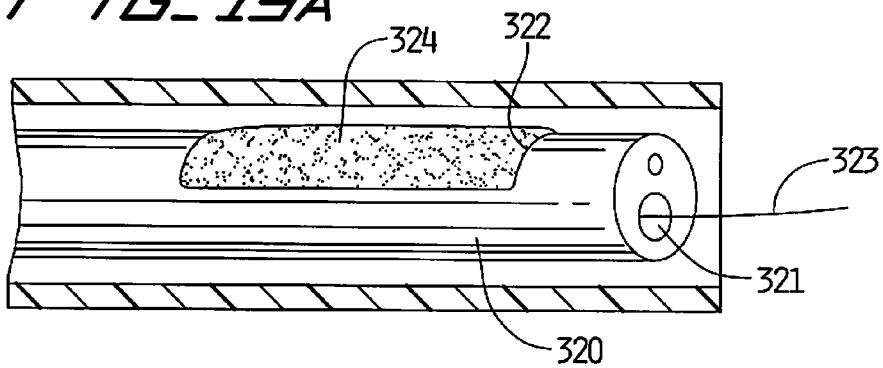
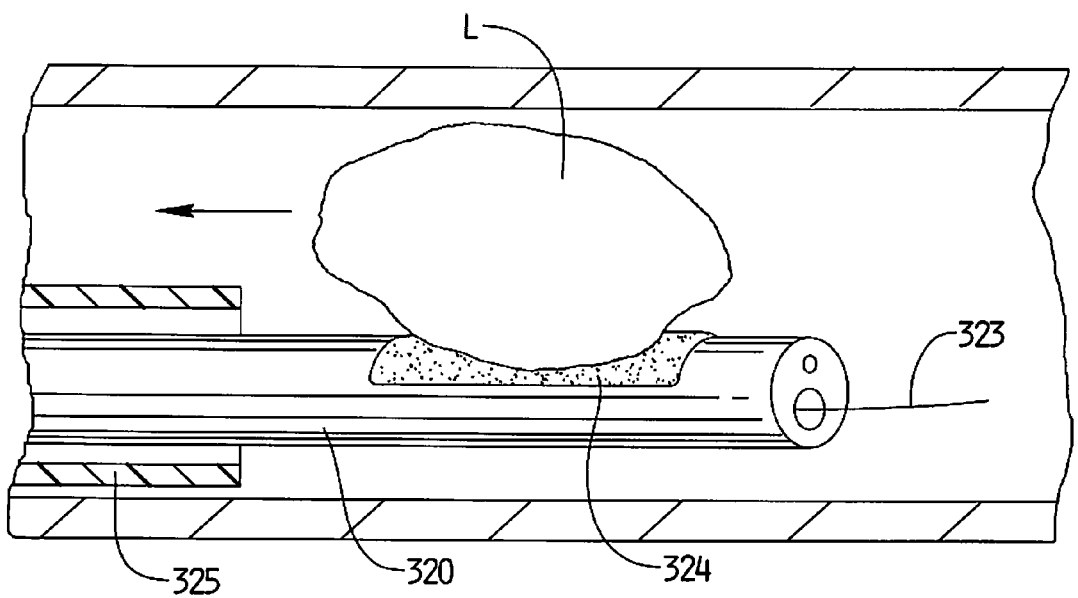

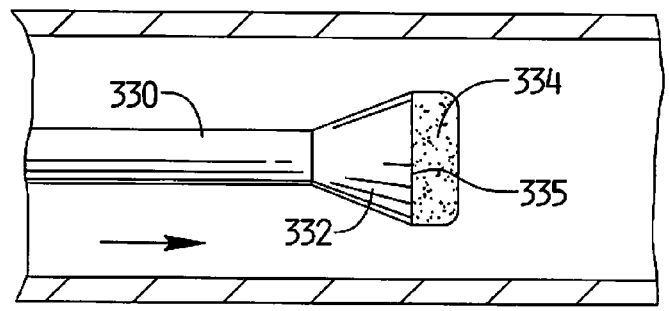
FIG_20A
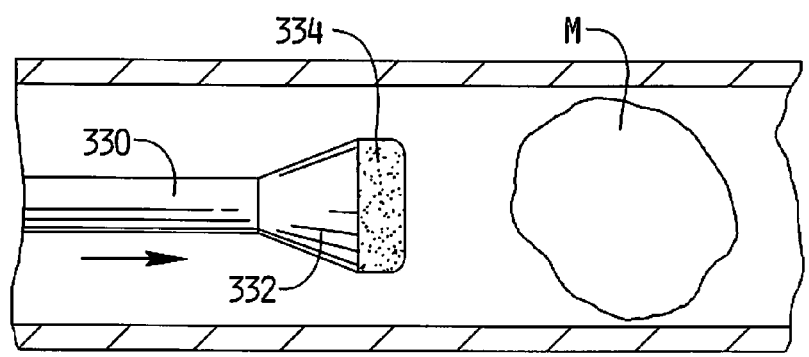
FIG_20B
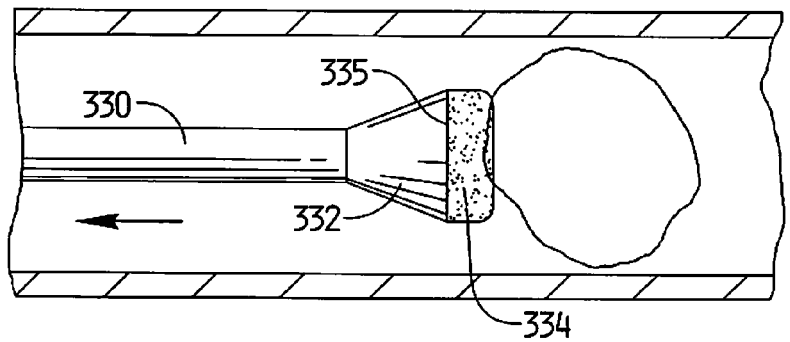
FIG_20C

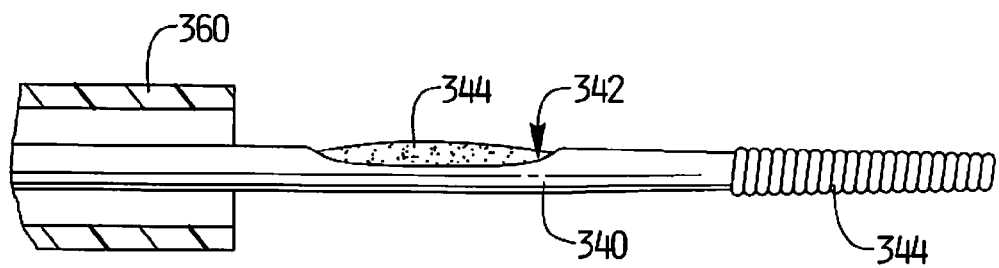
FIG_21
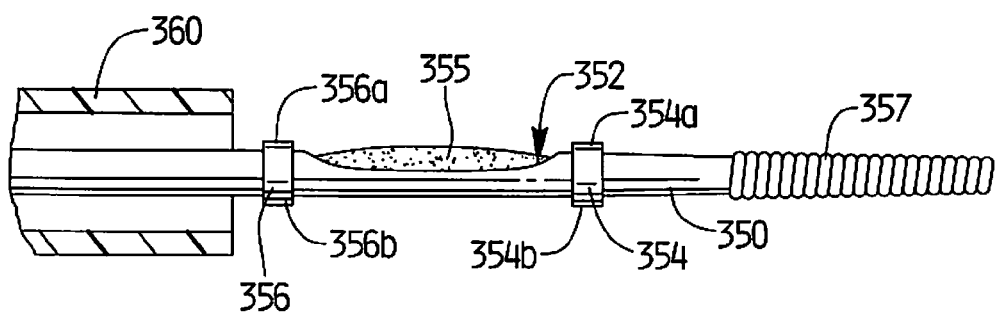
FIG_22
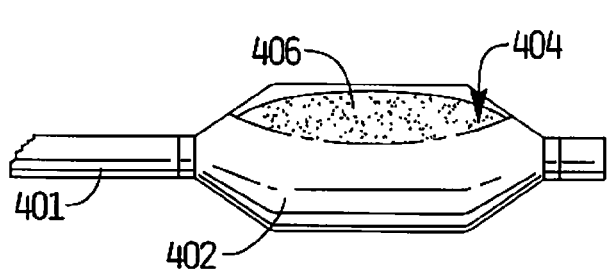
FIG_23A
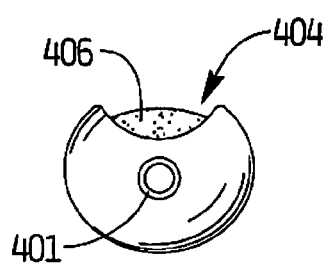
FIG_23B

FIG_24A
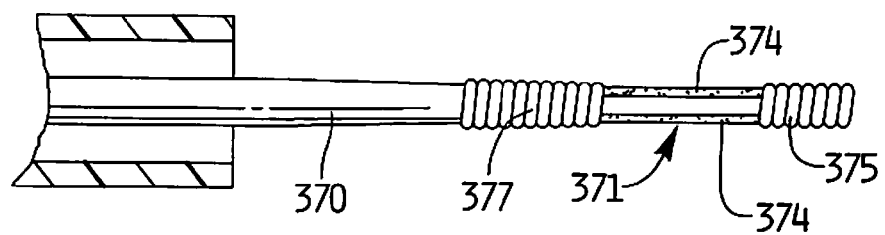
FIG_24B
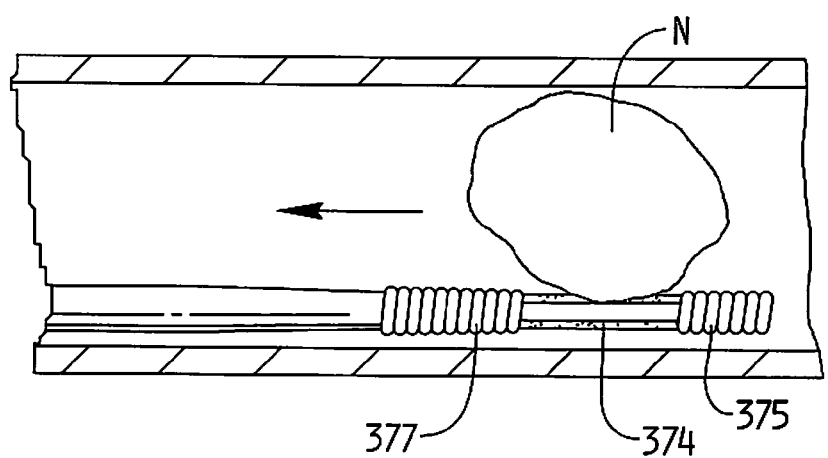

CLOT RETRIEVAL DEVICE

This application claims priority from provisional application Ser. No. 60/799,055, filed May 9, 2006, the entire contents of which are incorporated herein by reference.

BACKGROUND

1. Technical Field

This application relates to medical devices for removing plaque, clot or other material from the body or for retrieving foreign bodies from the body.

2. Background of Related Art

Currently there exists various mechanical devices for removing a clot from vessels. One current device is in the form of a corkscrew which is twisted into the clot and then pulled out with the clot engaged. Another known device utilizes several jaws which clamp onto the clot to remove the clot.

These devices suffer from several disadvantages due in part to the fact that clots are not uniform. In addition to varying size and being irregularly shaped, clots vary in their softness/calcification. In fact, this variation in hardness can exist within the clot itself, with some regions being more calcified than others. Due to this variation, a one size mechanical removal device is not always effective in removing the clot. In addition, if not properly grasped, the clot can become detached during the removal procedural, dangerously causing the clot to enter the bloodstream.

The need therefore exists for an improved device for removing clot or other body material from the vascular system. It would be advantageous if such device reduced the likelihood of the clot detaching from the retrieval device during removal. It would also be advantageous if such device enhanced access to the clot.

SUMMARY

The present application overcomes the problems and deficiencies of the prior art. The present application provides a device for removing body material from a patient's body comprising a shaft and an adhesive carrying surface extending from the shaft. The adhesive carrying surface is movable with respect to the shaft from an insertion position to an engagement position. An adhesive is on at least a portion of the outer surface, and of sufficient stickiness to adhere to the body material to remove the material when the shaft is removed from the patient's body.

In one embodiment, the adhesive carrying surface comprises a balloon. In one embodiment, the proximal surface of the balloon contains the adhesive to adhere to a distal portion of the body material to be removed. In another embodiment, the adhesive carrying surface comprises first and second movable arms, wherein the adhesive is on a surface portion of the arms. In one embodiment, the arms are formed from a shape memory tube cut into sections.

In one embodiment the adhesive carrying surface comprises at least one arm extending from the shaft wherein the arm is movable with respect to the shaft from a first open position more in line with the shaft to a second position at a greater angle to the shaft to engage body material. In one embodiment, the arm extends toward the proximal end of the shaft.

In an alternate embodiment, the device further comprises a mesh positioned distal of the adhesive carrying surface wherein the mesh is expandable to engage the body material. A portion of the region between the mesh and the adhesive carrying surface can also have an adhesive material thereon.

In an alternate embodiment the adhesive carrying material comprises an expandable mesh.

The present invention also provides a device for removing material from a patient's body comprising an elongated member having a cutout formed therein and an adhesive on at least a portion of an outer surface of the cutout area. The adhesive has sufficient stickiness to adhere to the body material to remove the material when the shaft is removed from the patient's body.

In one embodiment, the elongated member is a guidewire or hypotube. In another embodiment, the elongated member is a catheter. Optionally, at least one spacer can be provided extending from the elongated member to keep the adhesive out of contact with the vessel wall.

BRIEF DESCRIPTION OF DRAWINGS

Preferred embodiments of the present invention are described herein with reference to the drawings wherein:

FIG. 1A is a side view of a first embodiment of the balloon catheter of the present invention showing the balloon with adhesive on its surface in the collapsed (deflated) condition within the delivery sheath;

FIG. 1B shows the balloon of FIG. 1 exposed from the delivery sheath and in the expanded inflated condition.

FIGS. 1C-1G illustrate use of the catheter of FIG. 1 to remove plaque from the vessel, wherein FIG. 1C is a side view of the vessel showing plaque on the vessel wall;

FIG. 1D shows the catheter with deflated balloon being inserted to cross the lesion so the balloon is in the area of the vessel containing the plaque;

FIG. 1E shows the sheath retracted and the balloon being inflated so the adhesive engages and attaches to the plaque;

FIG. 1F shows the balloon inflated and the adhesive engaging and adhering to the plaque; and FIG. 1G shows the balloon deflated and being withdrawn with some of the plaque attached to the balloon.

FIG. 2A is a side view of an alternate embodiment of the present invention showing a spherical balloon with an adhesive on its surface in the collapsed condition within the delivery sheath;

FIG. 2B illustrates the balloon of FIG. 2A in the expanded (inflated) condition exposed from the delivery sheath;

FIGS. 3A and 3B are side views showing alternate embodiments of a balloon having an adhesive on its surface, the balloon shown in the inflated condition;

FIGS. 4A and 4B are other alternate embodiments of a balloon having an adhesive, the balloon shown in the inflated condition;

FIGS. 5-8 illustrate an alternate embodiment of the present invention having arms with an adhesive, wherein FIG. 5 is a side view of the arms in the collapsed position (condition) within a delivery sheath;

FIG. 6A is a side view showing the arms advanced distal of the sheath and in the expanded position;

FIG. 6B is a front view of the arms of FIG. 6A;

FIG. 7 shows the device engaging a proximal portion of the clot in the vessel; and FIG. 8 shows the clot attached to the arms and being removed from the vessel.

FIGS. 9-12 illustrate another alternative embodiment of the present invention having proximally facing arms with adhesive, wherein FIG. 9A is a side view showing the arms released from the cover and in the open position;

FIG. 9B is a front view of the arms of FIG. 9A;

FIG. 10 shows the open arms positioned distal of the clot in the vessel;

FIG. 11 shows the device engaging the clot with the cover being retracted to engage the arms; and FIG. 12 shows the clot attached to the adhesive surface of the arms and being removed from the vessel.

FIG. 13A is a side view of an alternative embodiment of the arms of FIG. 6 having two arms with adhesive and a series of teeth formed on the clot engaging surface of the arms, the arms shown in the open position;

FIG. 13B is a front view of the arms of FIG. 13A;

FIGS. 14A-14C illustrate another alternate embodiment of a material retrieval device of the present invention, wherein FIG. 14A shows the anchor and mesh of the device in the collapsed position;

FIG. 14B shows the anchor and mesh in the expanded position; and

FIG. 14C shown the clot attached between the anchor and mesh by adhesive.

FIG. 15A illustrates an alternate embodiment of the present invention having a mesh structure with adhesive and a distal ball tip anchor, the mesh shown in the collapsed configuration;

FIG. 15B illustrates the mesh structure of FIG. 15A in the expanded configuration to enable the adhesive surface to attach to the plaque;

FIG. 16 illustrates an alternate embodiment of the mesh structure of FIG. 15A having cutting blades, the mesh shown in the expanded position;

FIG. 17 illustrates an alternate embodiment of the present invention having a balloon with adhesive and a catheter with a curved tip;

FIG. 18A is a side view of a catheter of the present invention having adhesive (glue nodules) on its outer surface;

FIG. 18B is a front view of the catheter of FIG. 18A;

FIG. 19A illustrates a side view of a dual lumen catheter of the present invention having one of its lumens cut away to create a region for adhesive;

FIG. 19B shows the catheter of FIG. 19A engaging a clot with its adhesive for withdrawal from the vessel;

FIGS. 20A-20C are side views of a catheter of the present invention having an adhesive at the flared end, wherein FIG. 20A shows the catheter being advanced in the vessel;

FIG. 20B shows the catheter being further advanced to a position adjacent a clot; and FIG. 20C shows the adhesive engaging a proximal surface of the clot for withdrawal of the clot.

FIG. 21 is a side view of a hypotube of the present invention having a portion cut away to create a region for adhesive;

FIG. 22 is an alternate embodiment of the hypotube of FIG. 21 having a pair of spacers;

FIG. 23A is a side view of another alternate embodiment of the present invention having a balloon with a portion removed to create a region for adhesive;

FIG. 23B is a front view of the device of FIG. 23A;

FIG. 24A is a side view of a guidewire of the present invention having a reduced diameter portion to create a region for adhesive;

FIG. 24B illustrates the device of FIG. 24A engaging a clot with the adhesive for removal from the vessel;

FIGS. 25A-25C illustrate an alternate embodiment of the guidewire of the present invention having a clamping arm and a reduced diameter region to receive adhesive, wherein FIG. 25 shows the arm cover in the retracted position to maintain the arms in a closed position;

FIG. 25B shows the clamping arm exposed from the cover and in an open position to engage clot in the vessel; and FIG. 25C shows the adhesive attached to the clot and the clamping arm clamping the clot for withdrawal from the vessel.

DESCRIPTION OF THE PREFERRED EMBODIMENTS

Figure 25A:
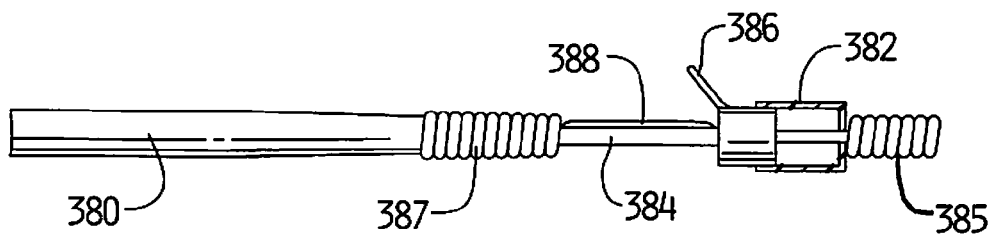

In the drawings, wherein like reference numerals identify similar or like components throughout the several views, various embodiments of medical devices of the present invention are described for removing plaque, clots or other materials from the body, and more particularly from blood vessels. The devices can also be used for retrieving foreign bodies such as stents, coils and filters. In general, each of the devices of the present invention has an element with a "sticky" material on at least part of its surface which engages the body material so it adheres or attaches thereto. Once adhered, the device is removed from the vessel, carrying the material with it. The devices herein are shown by way of example withdrawing a particular material, e.g. blood clot or loose plaque. It should be understood that each of these devices can be used to remove/retrieve other body materials, such as kidney stones or foreign materials as well. The term "adhesive" as used herein is to define a biocompatible "sticky" substance that adheres or attaches to the material to be removed with sufficient force so it can be removed. Examples of adhesive material can include, cyanoacrylate, hydrogel and fibrin glue, or a combination of these materials, although it is contemplated that other sticky materials could be utilized. Additionally, a wet adhesive can be used so the surface is sticky when inserted to the desired surgical site or a time release adhesive can be utilized so the adhesive will be released or activated from the surface after a predetermined amount of time, or activated by the addition of an activator to the treatment site. The adhesive can be in the form of a coating placed by methods such as spraying or dipping. Other methods of attaching the adhesive are also contemplated.

In some embodiments the adhesive is shown covering an entire surface. It should be appreciated that the adhesive can be placed over only a portion of the surface, or placed intermittently on the surface, so long as there is sufficient adhesive to perform the function of attaching the material for retrieval from the body.

In certain embodiments, the medical device includes a balloon, mesh or other structure radially extending from a catheter which contains the "sticky" material, which could also be of varying degrees of adhesion on the device. In other embodiments, the catheter itself contains the adhesive material. In still other embodiments, designed to provide a lower profile, a portion of a guidewire or hypotube contains the adhesive. These various embodiments are discussed below in detail.

The device can be advanced through a PTCA catheter, a microcatheter, or delivery sheath, or alternatively, not inserted through any other device and used as a stand alone device as it is inserted to the treatment area.

In the embodiments of FIGS. 1-5, a balloon is utilized to withdraw the material. More particularly, in FIGS. 1A-1B, the device (catheter) includes sheath 12, shaft 14 and balloon 16 attached to the shaft. Radiopaque marker bands, such as bands 13 and 15, can be provided on the shaft or the balloon for visualization. An adhesive material 19 is placed on the outer surface 17 of the balloon. Although adhesive 19 is shown extending along the entire surfaces 17a, 17b, it is also contemplated that it extends only along part of the surfaces or extends on the illustrated angled surfaces, or even over the entire outer surface of the balloon. The balloon 16 is shown in the collapsed position in FIG. 1A within delivery sheath 12. When advanced from the sheath, or the sheath 12 is retracted (or both moved relative to each other), the balloon can be inflated to expand to the position of FIG. 1B.

Alternate configurations of the balloon are illustrated in FIGS. 2A and 2B. In FIG. 2A, the collapsed balloon 26, attached to shaft 24, is in the deflated state within sheath 22 for insertion. Relative movement of the sheath 22 and shaft 24, i.e. proximal movement of the sheath 22, distal movement of shaft 24, or movement of both in opposite directions, exposes the balloon 26 for expansion (inflation) as shown in FIG. 2B to an engagement position. Adhesive 29 is shown covering the entire exterior surface, although as explained above with respect to all embodiments herein, covering less of the exterior surface with an adhesive coating is also contemplated.

In FIG. 3A, a conical shaped balloon 36 on shaft 34 has adhesive 39 on a proximal surface 37. The balloon is pulled back proximally so the proximal surface engages and sticks to a distal portion of the material to be removed. The balloon 36 is then further retracted to pull out the material which is adhered to surface 37. In FIG. 3B, the proximal tapered or angled outer surfaces 47, 48 of balloon 46 have adhesive 49. The adhesive on these surfaces 47, 48 engage and adhere to a distal portion of the material to be removed. The adhesive could optionally be on the distal surface of balloon 36 and 46 to attach to a proximal portion of the clot or other material to be removed. As mentioned above, as in the other embodiments disclosed herein, the adhesive can be placed on the entire surface or only part of the surface of the balloon or other structure.

Adhesive 59 is placed on the outer surfaces of the different balloon configurations 50, 52 of FIGS. 4A-4B. Coating all or only select parts of the exterior surfaces of the balloons of FIGS. 3A-4B is contemplated.

Use of the adhesively coated balloon to remove plaque will now be described in conjunction with the embodiment of FIG. 1 by way of example. FIG. 1C illustrates plaque P extending from the vessel wall W. The catheter 10 is inserted through the vascular system over guidewire 11 until the balloon 16, with adhesive 19, is aligned with the plaque to be removed as shown in FIG. 1D. The sheath 12 is withdrawn exposing balloon 16, which is subsequently inflated to engage and loosen the plaque. The adhesive 19 engages the loose plaque as shown in FIG. 1F, the balloon 16 is deflated, with the loose plaque P2 attached to the balloon 16 as it sticks to the adhesive 19, and the catheter 10 with loose plaque is removed in the direction of the arrow as shown in FIG. 1G.

FIGS. 5-13B illustrate alternate embodiments of the present invention utilizing expandable arms with adhesive coating to retrieve the material from the body. Turning first to FIGS. 5-8, shape memory tube 100, preferably made of Nitinol (although other shape memory materials such as platinum or shape memory plastic are contemplated), is cut at its distal end into quarter sections to form four arms 102a, 102b, 102c and 102d. Initially, when inside the delivery sheath 104 for insertion, the arms 102a-102d are maintained in more of a closed position. When exposed from the sheath 104, either by movement of the sheath 104, tube 100, or both, the arms 102a-102d return to their open shape memory position as shown in FIGS. 6 and 7. The outer surface of arms 102a-102d has adhesive material 106. As shown in FIG. 7, the arms 102a-102d are advanced to clot C. When engaged with the proximal portion of clot C within vessel V, the clot adheres to adhesive 106 and the tube 100 is withdrawn from the vessel, in the direction of the arrow of FIG. 8. Optionally, depending on the collapsibility of the clot, tube 100 can be withdrawn through the sheath 104, to remove the clot. The sheath 104 could optionally be advanced prior to removal to provide a clamping force on the arms 102, to enhance retention of the clot (or other material).

Optionally, the arms of the cut tube can include a series of teeth to enhance their grasping of the clot. Also, optionally, instead of being formed into quarters, the tube can be cut into halves to form two arms. This is shown for example in FIGS. 13A and 13B which has both these features. Shape memory tube 110 is cut at its distal end into half to form two arms 112 and 114. Each arm has a series of teeth 115 formed on surface 116. Surface 116 also has an adhesive surface 119 (removed for clarity in FIG. 13b). This device functions in a similar manner as the device of FIG. 6. (Other numbers of arms are also contemplated).

In the embodiment of FIGS. 9-12, tube 120 is cut to form two rearwardly facing arms 122 and 124. The arms 122 and 124 open in the proximal direction. Adhesive 126 is placed on the inner surface 125 of the arms. Adhesive 126 can also optionally be placed on outer surface 121 of tube 120. Cover or sheath 128 is attached to tube (or wire) 132. When arms 122 and 124 are contained within the sheath 128, (for insertion) they are in a more closed position with the arms closer to the tube. When the arms 122 and 124 are no longer constrained by cover 128, the arms move to their shape memory position as shown in FIG. 9A.

In use, the device 100 is advanced in the vessel with the arms 122, 124 within cover 128 so that the region of the tube 120 containing the arms is positioned past clot D as shown in FIG. 10. The sheath 128 is either advanced from the arms 122, 124 or the tube 120 with arms 122 and 124 is retracted from the sheath, or both are moved away from each other. This relative movement exposes arms 122 and 124 and enables them to move to their shape memory open position. The device is retracted so the adhesive 126 engages a distal portion of clot D. Cover 128 is then retracted by retraction of tube 132 to force the arms 122, 124 towards their closed position, as shown in FIG. 11, to provide additional clamping force on the clot. The device 100 is then retracted through the vessel, in the direction of the arrow of FIG. 12, with the clot adhered to arms 122, 124 for removal.

FIGS. 14A-14C illustrates an alternate embodiment for capturing the clot between an expandable mesh structure and a pair of arms. More particularly, catheter 200 includes an outer tube 202, preferably composed of shape memory material such as Nitinol (although other shape memory materials are contemplated), cut at its distal end to form two arms 203, 204. Arms 203, 204 have an adhesive 208 on their inner surface 213. A wire (or tube) 206 extends through the outer tube 202 and is attached to ball tip 207 of inner tube 209. A mesh structure 210 is positioned proximal of the ball tip 207 and attached to inner tube 209, or formed integrally with tube 209. An outer sheath 218 maintains the arms 202, 204 in the closed (collapsed) position.

In use, the device 200 is moved relative to the sheath 212 to expose the two arms 203, 204, allowing them to expand radially to their shape memory position as shown in FIG. 14B. Wire 206 is retracted, thereby pulling ball tip 207 rearwardly, and compressing the mesh structure 210 so it expands radially. (Alternatively, the outer tube 202 could be pushed forward to compress the mesh with the inner tube attached to the outer tube 202 at its distal end.) Mesh structure 210 has an adhesive 212. Region 209 of tube 206 can also have an adhesive. As shown in FIG. 14C, clot E adheres to the region 209 of the tube, as well as to proximal surface 211 of mesh 210 and surface 213 of arms 203, 204 due to the adhesive. The clot E is also captured, and even in certain instances compressed, between the mesh 210 and arms 203, 204 to provide additional grasping force on the clot to facilitate removal.

In the embodiment of FIGS. 15A, 15B a mesh or stent 210 like structure 230 has an adhesive material 236 on its outer surface. The mesh 230 is attached at a distal end to the ball tip 234. The adhesive can be placed on all or part of the outer surface. Retraction of wire 232 moves ball tip 234 proximally, thereby compressing the mesh 230 and forcing it to expand radially so the adhesive 236 can engage the clot F. The device is shown in FIG. 15A inserted through sheath 321.

In the embodiment of FIG. 16, mesh structure 240 has cutting blades 242 on its outer surface 245, designed to cut into plaque. Adhesive 243 is attached to the outer surface 245, and optionally to the blades 242 as well. The mesh is expanded by pull wire 247 in the same manner as in the embodiment of FIG. 15B. Alternatively, the cutting blades can be placed on a balloon with the balloon and/or blades having an adhesive.

In FIG. 17, catheter 260 has a curled or angled tip 262. Balloon 264 has an adhesive 266 on its outer surface. Curled tip is placed through the obstruction and the balloon is inflated. The clot is wedged between the inflated balloon 264 and the curled tip 262 to further grasp the clot adhesively attached to the balloon 264.

FIGS. 18-25 illustrate another approach to removing clots or other material by use of adhesive in which the adhesive is placed on the catheter or guidewire itself.

In FIGS. 18A and 18b, glue nodules 302 are placed on the outer surface 303 of catheter 301. The glue 302 adheres to the clot so removal of the catheter carries the clot from the body. In an alternate embodiment, catheter 301 could be used as an outer covering placed over a guidewire or other catheter, and secured thereto.

Adhesive can be applied to a skived or cut out region of the catheter, as shown for example in FIGS. 19A, 19B. Dual lumen catheter 320, having lumen 321 for receiving guidewire 323, has a cut out region 322 formed in its side wall. Adhesive material is placed in this cutout area 322, forming a side "sticky" region. The catheter 320 is placed underneath or above the clot, depending on the clot location and orientation, so the region 322 is aligned with a respective bottom or top portion of the clot. The adhesive region 324 is then moved into contact with the clot L so that it adheres to the adhesive, and the catheter is withdrawn in the direction of the arrow, optionally through sheath 325 (depending on clot collapsibility), carrying the attached clot L from the body.

Adhesive can alternatively be applied to the distal end of the catheter so the clot can be contacted from its proximal end portion, rather than underneath or above as in FIG. 19. This is shown for example in FIGS. 20A-20C, wherein catheter 330 has a flared end 332 to create an enlarged surface area 335. Adhesive 334 is attached to the distal surface area 335. The catheter 330 is advanced to the clot M until its adhesive covered distal end surface is in contact with a proximal end portion of the clot M. The catheter 330 is withdrawn as shown in FIG. 20C carrying attached clot M.

In the alternate embodiments of FIGS. 21, 22 and 24, a guidewire or hypotube has an adhesive area, thereby creating a lower profile for clot, plaque or other material retrieval. This is beneficial in cerebral application as well as other applications. The adhesive can be placed directly on the wire or hypotube, or on a transition tube positioned thereover. More particularly, in FIG. 21, cut out area 342 of guidewire 340 (or alternatively a hypotube) contains adhesive 344. This cut out area is positioned proximal of the coiled tip 344 of the guidewire 340. To keep the adhesive out of contact with the vessel wall, optionally a pair of spacers could be provided as shown in FIG. 22. Proximal spacer 356 is positioned proximal of cut out area 352 and distal spacer 354 is positioned distal of the cut out area. Both spacers are proximal to the coiled tip 357. In this manner, the top and bottom surfaces 354a, 354b and 356a, 356b, have a dimension larger than the cross-sectional dimension (or diameter) of guidewire 350. Since the plaque or clot extends from the vessel wall, the adhesive 355 can engage the extending portion of the clot without contacting or with minimal contact of the vessel wall. The spacers 354, 356, also reduce the likelihood of vessel wall contact by the adhesive once the guidewire is exposed from sheath 360 and is manipulated in the vessel to the desired site. Spacers can also be provided on the catheter of FIG. 19.

In FIGS. 24A, 24B, the adhesive 374 is placed on a reduced diameter region 371 of the guidewire 370, formed between distal and proximal coils, 375, 377, respectively. Clot N is engaged by the adhesive 374 and the guidewire 370 with attached clot is withdrawn in the direction of the arrow of FIG. 24B.

Figure 25B:
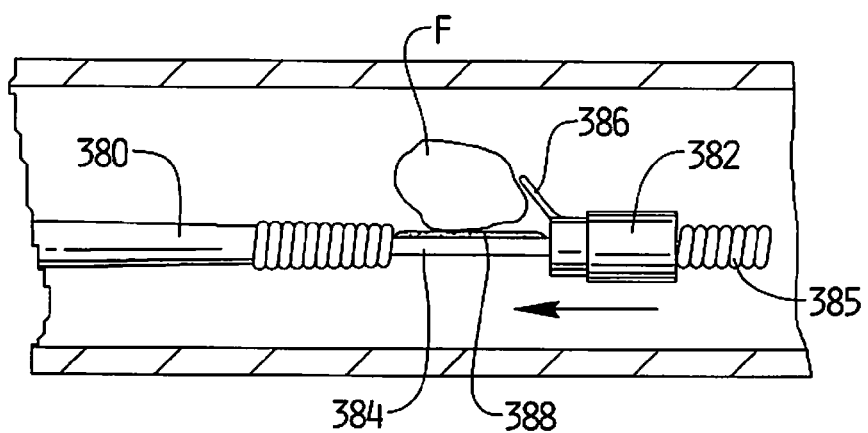
Figure 25C:
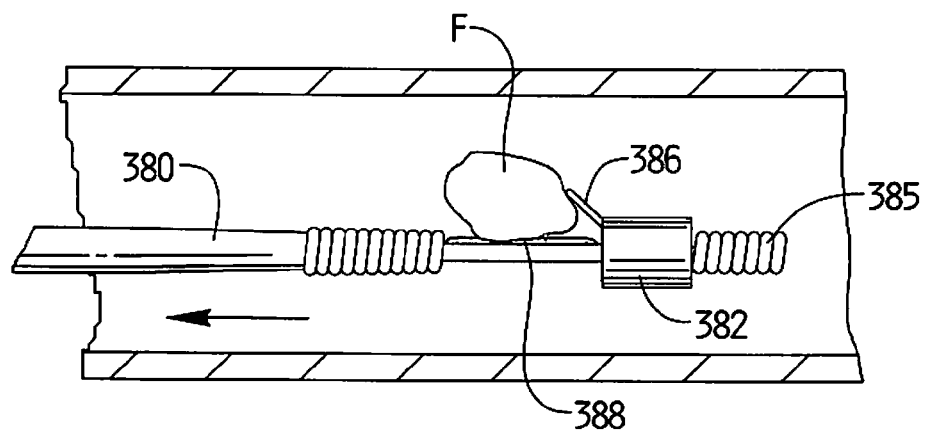

In the alternate embodiment of FIGS. 25A-25C, clamping arms 386 are released by cover 382 in the same manner as in the embodiment of FIG. 9. This embodiment differs from that of FIG. 9 in that instead of adhesive on a catheter, adhesive is placed on a guidewire, and more specifically the reduced diameter region 384 of guidewire 380. Region 384 is between distal and proximal coils 385, 387. Cover 382 is retracted to move clamping arms 386 towards a closed position to clamp clot F as shown in FIG. 25C. Adhesive 388 can also optionally be placed on clamping arms 386.

In the embodiment of FIGS. 23A, 23B, a balloon 402, mounted on catheter shaft 401, has a cut out region 404. Adhesive 406 is placed in the cutout region. As in previously described embodiments, the cutout region reduces undesired contact of the adhesive with the vessel wall as it isolates the adhesive from the wall.

While the above description contains many specifics, those specifics should not be construed as limitations on the scope of the disclosure, but merely as exemplifications of preferred embodiments thereof. For example, although multiple arms are shown, a single arm is also contemplated. Also, although shown as removing a clot, other material can also be removed. Neurovascular, cardiovascular as well as other applications are contemplated. Those skilled in the art will envision many other possible variations that are within the scope and spirit of the disclosure.

What is claimed is:

1. A device for removing body material from a patient's body comprising a shaft, the shaft having a proximal portion and a distal portion and a longitudinal axis, an adhesive carrying surface extending at an acute angle to the longitudinal axis and facing the proximal portion of the shaft, and being movable with respect to the shaft from an insertion position to an engagement position and having an adhesive exposed on at least a portion of an inner surface, the adhesive extending along a length of the adhesive carrying surface and having sufficient stickiness to adhere to the body material to remove the material when the shaft is moved in a proximal direction so the adhesive carrying surface moves in a proximal direction to come into contact with the body material and the shaft is removed from the patient's body.

2. A device for removing body material from a patient's body as recited in claim 1, wherein the adhesive carrying surface comprises a balloon.

3. A device for removing body material from a patient's body as recited in claim 2, wherein the balloon has a distal and proximal surface, and the proximal surface of the balloon contains the adhesive to adhere to a distal portion of the body material to be removed.

4. A device for removing body material from a patient's body as recited in claim 1, wherein the adhesive carrying surface comprise first and second arms, the adhesive being on at least a portion of an inner surface of the arms.

5. A device for removing body material from a patient's body as recited in claim 4, wherein the arms are formed from a shape memory tube cut into sections to form the arms.

6. A device for removing body material from a patient's body as recited in claim 5, further comprising teeth on at least one of the arms.

7. A device for removing body material from a patient's body as recited in claim 1, wherein the adhesive carrying surface comprises at least one arm extending from the shaft, the arm movable with respect to the shaft from a first open position more in line with the shaft to a second position at a greater angle to the shaft to engage body material.

8. A device for removing body material from a patient's body as recited in claim 7, wherein the shaft has a proximal end closer to the user and a distal end further from the user, and the arm extends toward the proximal end.

9. A device for removing body material from a patient's body as recited in claim 1, further comprising a mesh positioned distal of the adhesive carrying surface, the mesh expandable to engage the body material.

10. A device for removing body material from a patient's body as recited in claim 9, wherein at least a portion of the region between the mesh and the adhesive carrying surface has an adhesive material thereon.

11. A device for removing body material from a patient's body as recited in claim 1, wherein the adhesive carrying material comprises an expandable mesh.

12. A device for removing material from a patient's body comprising an elongated member having a longitudinal axis defining a longitudinal dimension extending from a proximal portion to a distal portion, a first transverse dimension transverse to the longitudinal axis, and a cutout formed therein, the cutout forming a cutout area having a second transverse dimension transverse to the longitudinal axis and being less than the first transverse dimension, and an adhesive exposed on at least a portion of an outer surface of the cutout area, the adhesive having sufficient stickiness to adhere to a body material to remove the body material when the shaft is removed from the patient's body.

13. A device for removing body material from a patient's body as recited in claim 12, wherein the elongated member is a guidewire or hypotube.

14. A device for removing body material from a patient's body as recited in claim 12, wherein the elongated member is a catheter.

15. A device for removing body material from a patient's body as recited in claim 14, further comprising a first spacer extending from the elongated member to keep the adhesive out of contact with the vessel wall.

16. A device for removing body material from a patient's body as recited in claim 15, further comprising a second spacer spaced distally from the first spacer, the adhesive positioned between the first and second spacers, and the first and second spacers have a transverse dimension larger than the first transverse dimension of the elongated member proximal and distal of the first and second spacers.

17. A device for removing body material from a patient's body as recited in claim 12, wherein the elongated member comprises a balloon, the cutout forming a concave surface in the balloon to support the adhesive below an outer surface of the balloon.

* * * * *